United States Patent [19]

Kalmbach

[11] 4,277,637
[45] Jul. 7, 1981

[54] PROCESS FOR PURIFYING ARYL-SUBSTITUTED MONO-OLEFINS

[75] Inventor: Debra S. K. Kalmbach, Midland, Mich.

[73] Assignee: The Dow Chemical Company, Midland, Mich.

[21] Appl. No.: 868,012

[22] Filed: Jan. 9, 1978

[51] Int. Cl.³ .............................................. C07C 7/12
[52] U.S. Cl. .................................................. 585/828
[58] Field of Search ................... 260/669 A; 585/820, 585/828

[56] References Cited

U.S. PATENT DOCUMENTS

| 3,409,691 | 11/1968 | Small | 260/676 |
| 3,922,217 | 11/1975 | Cohen et al. | 260/674 S A |
| 3,969,344 | 7/1976 | Ackermann et al. | 260/669 A |

FOREIGN PATENT DOCUMENTS 495023  11/1938  United Kingdom ................ 260/669 A

OTHER PUBLICATIONS

R. Kunin, *Ion Exchange Resins*, pp. 255–259 (1972).

*Primary Examiner*—Delbert E. Gantz
*Assistant Examiner*—Joseph A. Boska
*Attorney, Agent, or Firm*—Charles J. Enright

[57] ABSTRACT

α-Alkylstyrene impurities, such as isopropenylstyrene, are removed from styrene and nuclear alkyl derivatives of styrene, such as t-butylstyrene, containing the same by treatment with a strong acid cation exchange resin.

10 Claims, No Drawings

PROCESS FOR PURIFYING ARYL-SUBSTITUTED MONO-OLEFINS

BACKGROUND OF THE INVENTION

New techniques for separating mixtures of polymerizable monomers are widely sought. In the chemical industry, a high degree of purity in substances which are subjected to polymerization is necessary insofar as it permits the preparation of polymers of high molecular weight, a high reactivity of the polymerization system, a high yield of polymer, and a low consumption of catalyst. It is also necessary to control the influence of various impurities on the characteristics of the polymers. For example, as an impurity in t-butylstyrene, isopropenylstyrene is a polyfunctional monomer and acts as a cross-linking monomer when the t-butylstyrene is polymerized. For use as a polymerization monomer, it is desirable and usually specified that the t-butylstyrene contain not more than, and preferably less than, 50 ppm of isopropenylstyrene.

Various techniques have been suggested for purifying monomers, such as fractional or extractive distillation, crystallization and zone-wise fusion, extraction and treatment with compounds which react with some impurities in the monomers. Until now, there has been no acceptable way to remove small amounts of $\alpha$-alkylstyrene, especially amounts below about 5000 ppm, from mixtures of styrene and $\alpha$-alkylstyrene or derivatives thereof.

U.S. Pat. No. 2,215,569 teaches that mixtures of 25 percent styrene, 17-25 percent $\alpha$-alkylstyrene and 50-58 percent isopropylbenzene may be treated with sulfuric acid at about 70 percent to 90 percent strength at ordinary temperatures so as to effect the polymerization of the $\alpha$-alkylstyrenes leaving the styrene unchanged.

For the purpose of treating sytrene monomers containing $\alpha$-alkylstyrene impurities, sulfuric acid having a concentration in a range of about 70 percent to about 90 percent removed the $\alpha$-alkylstyrene impurities; however, continued contact with the sulfuric acid led to the polymerization of the desired styrenic monomer.

It is desirable to keep the concentration of impurities, such as $\alpha$-alkylstyrene and nuclear alkyl derivatives thereof, to a minimum, since they will react to form undesirable branched products in polymerization mixtures with styrene and nuclear alkyl derivatives of styrene. Further, it is particularly desirable to have the desired polymerizable styrene monomer in a high degree of purity since this will enhance the economics of production, sale and use. In accordance with the present invention, separation of mixtures of polymerizable aryl-substituted mono-olefins is obtained by contacting the mixture with an appropriate ion exchange resin. This process requires very low power consumption; avoids polymerization of the desired monomer; does not modify the properties of the desired monomer; limits loss of chemicals due to successive manipulations; avoids inconveniences due to washing, disposal of a deleterious waste stream, or use of extensive heat.

SUMMARY OF THE INVENTION

It has now been found that styrene and nuclear alkyl derivatives of styrene containing small concentrations of impurities such as $\alpha$-alkylstyrene and nuclear alkyl or alkenyl derivatives thereof can be treated to selectively remove the $\alpha$-alkyl compound by contacting the materials with the hydrogen form of a sulfonic acid cation exchange resin. The amount of $\alpha$-alkylastyrene impurity is not limited, although the treatment method is particularly advantageous when the starting materials contain from about 50 to about 5000 ppm of the $\alpha$-alkylstyrene compound, which are difficult to purify in any other way to provide styrene monomer suitable for polymerization to linear, non-cross-linked polymer. By this method, the $\alpha$-alkylstyrene compounds are selectively removed so that the resulting styrene product is essentially free of the $\alpha$-alkylstyrene impurity.

DETAILED DESCRIPTION OF THE INVENTION

This process comprises contacting a starting monomer mixture containing at least one styrenic monomer and at least one $\alpha$-alkylstyrene impurity with specified ion exchange resin material, usually in the conventional form of beads. The materials can be brought into contact in conventional ways in a batchwise or continuous manner.

In some embodiments, beads of selected resin are added to a batch of starting monomer; the mixture is then stirred until the desired benefit is effected, and the treated monomer is separated from the resin beads by decantation or filtration. In other embodiments, a stream of starting monomer is passed into and through a treatment zone containing a fixed bed of resin in the form of discrete particles, such as beads, to provide an effluent stream of treated monomer.

By "styrenic monomer" is meant styrene and nuclear alkyl derivatives of styrene. By "$\alpha$-alkylstyrene impurity" is meant $\alpha$-alkylstyrenes and nuclear alkyl and alkenyl derivatives of $\alpha$-alkylstyrene.

Specific examples of styrenic monomers are styrene and ar-arlkylstyrenes such as vinyltoluene, vinylxylene, ethylstyrene, propylstryene, isopropylstyrene, butylstyrene, t-butylstyrene, pentylstyrene, hexylstyrene, heptylstyrene, octylstyrene, and the like in their various isomeric forms.

Specific examples of $\alpha$-alkylstyrenes, which, as impurities in styrenic monomers, can be removed by treatment in accordance with this invention, include $\alpha$-methylstyrene, $\alpha$-ethylstyrene, and ar-alkyl-$\alpha$-alkyl-styrenes and ar-alkenyl-$\alpha$-alkylstyrenes such as alkyl-$\alpha$-methylstyrene, t-butyl-$\alpha$-methylstyrene, ethyl-$\alpha$-methylstyrene, isopropenylstyrene, and the like in their various isomeric forms.

Starting mixtures containing two or more styrenic monomers and/or two or more $\alpha$-alkylstryene impurities can also be beneficially treated in accordance with this invention.

This invention is particularly applicable for the removal of isopropenylstyrene impurity from t-butylstyrene.

The ion exchange resin material preferably used for the process according to the invention includes macroporous cation exchangers containing sulfonic acid groups which are based on styrene-divinylbenzene copolymers.

It has proved to be of advantage to use macroporous cation exchanger resins in the form of small spheroidal beads of predominantly 10 to 500, preferably 20 to 50 mesh size, the resin having an average porosity of at least about 5 percent, an average specific surface area of from about 5 to about 800 square meters per gram, and an average pore diameter of at least about 10 Angstrom units. Macroporous sulfonic acid cation exchange resins are made by sulfonication of macroporous cross-linked resins by any conventional sulfonation process for making cation exchangers. Suitable macroporous cross-linked resin materials and methods of making them are described in U.S. Pat. Nos. 2,974,178; 3,122,456 and RE 27,026, all of which are by reference hereby incorporated herein in their entirety. Such macroporous sulfonic acid cation exchange resins are obtainable commercially.

The moisture content of the macroporous cation exchange resins affects the activity rate of the resin on the removal of $\alpha$-alkylstyrene impurities from the starting styrenic monomer. Conventional water-swollen cation exchangers having from 40 to 50 percent moisture by weight of the wet resin are relatively inefficient for the present purpose. Macroporous sulfonic acid cation exchangers having lower moisture contents become increasingly more active as the moisture content is reduced, especially below about 40 percent water by weight of the dry resin. Those having moisture content below about 20 percent water based on dry resin are very active in removing $\alpha$-alkylstyrene impurity, but the time and conditions of contact between the resin and the starting styrenic monomer material must be monitored closely to avoid undesirable polymerization of the styrenic monomer. The present process is preferably carried out with macroporous sulfonic acid cation exchange resins having moisture content in the range from about 20 to about 30 weight percent water based on dry resin. Resins of reduced and controlled moisture content can be obtained from macroporous sulfonic acid cation exchange resins having larger moisture content by partial and controlled drying thereof by conventional means.

In general, the process is carried out with the starting monomers in the liquid phase at room temperature, although it can also be carried out at lower or higher temperatures which do not exceed the polymerization temperature of the desired stryene monomer or the thermal stability of the resin. The preferred temperature range for this reaction is from about 15° C. to about 35° C. An inert solvent may be present in, or added to, the starting monomeric material, if desired. Pressure is not a critical factor in the process and atmospheric or super atmospheric pressure may be employed.

When using a batch procedure, the treated liquid styrene monomer can be decanted or filtered from the resin beads and, using the same exchanger resin, the reaction vessel filled with more styrene mixture to be purified. In the continuous form of the process where the exchanger resin is in a fixed bed, the stream of the styrene mixture to be purified is pumped through the bed, preferably at a constant rate. By varying the temperature and catalyst load (or residence time), it is possible experimentally to determine the most favorable conditions for the particular starting materials by periodically collecting the effluent from the exchanger and determining the $\alpha$-alkyl impurity content thereof by analysis, e.g., by gas chromatography.

The following examples illustrate the invention but are not to be taken as limiting its scope. In the examples, quantities of material are expressed in terms of parts by weight, unless otherwise specified.

EXAMPLE 1

The strong acid macroporous sulfonic acid cation exchange resin used in this Example is made by the nuclear sulfonation of a copolymer of styrene and divinylbenzene in the form of beads about 20–50 mesh, has an average porosity of about 33 percent, an average specific surface area of about 57 square meters per gram, an average pore diameter of about 220 Angstrom units, and is in its $H^+$ form. The exchange resin is washed with water, washed with methanol, and air dried in a Buchner funnel overnight. The moisture content of the resulting resin is about 25 percent weight of water based on the weight of the dry resin. 11.4 Parts of the moisture-controlled resin are added to 85.7 parts of t-butylstyrene which contains 86 ppm of isopropenylstyrene. The mixture is placed in a vessel equipped with an agitator and continuously agitated at high speed. At the end of 7 hours, analysis of a sample by gas chromatography shows that the concentration of isopropenylstyrene in the treated t-butylstyrene has decreased below a concentration of 20 ppm.

EXAMPLE 2

In a manner similar to that used in Example 1, 61.4 parts of the same starting t-butylstyrene material is stirred with 9.75 parts of resin from the same batch of moisture-controlled resin used in Example 1. After 7 hours, the isopropenylstyrene is removed below 20 ppm.

EXAMPLES 3–6

Moisture Content Study

In these examples, the moisture content of a macroporous sulfonic acid cation exchange resin was varied to show the effect on the treatment of t-butylstyrene containing 86 ppm of isopropenylstyrene. A batch of commercial strong acid macroporous sulfonic acid cation exchange resin as described in Example 1 and containing 40 to 50 percent water based on the weight of wet resin was first dried substantially completely by heating for several days in a vacuum oven at 90° C. To portions of the resulting dry resin was then added water in various proportions as shown in Table I, and the resulting controlled-moisture resins were shaken with the starting t-butylstyrene monomer material.

The monomeric material being treated was sampled from time to time and tested for polymer formation using the dry Methanol test (ASTM Test No. D2121) by adding one part methanol to one part t-butylstyrene sample. Formation of a cloudy white precipitate was taken to indicate that some of the t-butylstyrene had polymerized. Several analyses were also made for isopropenylstyrene reduction by gas chromatography.

The results of the several runs conducted are reported in Table I below.

TABLE I

| | Example No. | | | |
|---|---|---|---|---|
| | 3 | 4 | 5 | 6 |
| Ion exchange resin, parts by weight | 0.5375 | 0.5547 | 0.5165 | 0.6104 |
| Water, parts by weight | 0.0478 | 0.1083 | 0.1824 | 0.2298 |
| t-Butylstyrene con- | | | | |

TABLE I-continued

| | Example No. | | | |
| --- | --- | --- | --- | --- |
| | 3 | 4 | 5 | 6 |
| taining 86 ppm iso-propenylstyrene, parts by weight | 3.6526 | 3.3936 | 3.2969 | 3.0778 |
| Moisture Content of Resin: (Weight of water based on dry resin) | 9% | 19.5% | 35.3% | 38% |
| Isopropenylstyrene (IPS) Reduction: | | | | |
| 1st Sampling | 1 hr - SPF* | 1¾ hr - No polymerization Some IPS reduction | 2½ hr - No polymerization No IPS reduction | 3½ hr - No polymerization No IPS reduction |
| 2nd Sampling | | 18 hr - SPF* | 36 hr - No detectable IPS | 44 hr - No detectable IPS |

*SPF - Significant polymer formation as determined by the dry Methanol test.

It is evident that the ion exchange resin in much more effective when the moisture content is in a range of from about 20 percent to about 30 percent weight of water based on dry resin. Significant polymer formation occurs when the moisture content is lower than the range suggested above. Resin having moisture content greater than about 30 percent weight of water based on dry resin functions relatively slowly in removing isopropenylstyrene.

What is claimed is:

1. A process for removing α-alkylstyrene, impurities of the group consisting of α-alkylstyrene, nuclear alkyl derivatives of α-alkylstyrene, and nuclear alkenyl derivatives of α-alkylstyrene, from starting mixtures thereof with at least one styrenic monomer of the group consisting of styrene and nuclear alkyl derivatives of styrene, which comprises contacting the starting mixture of styrenic monomer containing α-alkylstyrene impurities with a macroporous, sulfonic acid, $H^+$ form cation exchange resin containing moisture in the range of from about 20 percent to about 30 percent weight of water based on the weight of the dry resin.

2. The process of claim 1 wherein the α-alkylstyrene impurity is isopropenylstyrene.

3. The process of claim 1 wherein the styrenic monomer is t-butylstyrene.

4. The process of claim 1 wherein the resin is in the form of small spheroidal beads of predominantly 10 to 500 mesh size, the resin having an average porosity of at least about 5 percent, an average specific surface area of from about 5 to about 800 square meters per gram, and an average pore diameter of at least about 10 Angstrom units.

5. The process of claim 1 carried out in a batch manner.

6. The process of claim 1 carried out in a continuous manner by continuously passing a stream of the starting mixture through a treatment zone containing the cation exchange resin in the form of discrete particles.

7. The process of claim 1 wherein the starting mixture contains a predominant amount of the styrenic monomer.

8. The process of claim 1 wherein the starting mixture contains t-butylstyrene and from about 20 to about 5000 ppm of isopropenylstyrene and the resulting treated t-butylstyrene contains less than about 20 ppm of isopropenylstyrene.

9. The process of claim 8 wherein the resin is in the form of spheroidal beads of predominantly from about 20 to about 50 mesh size, has average porosity of at least about 5 percent, average specific surface area of from about 5 to about 800 square meters per gram, average pore diameter of at least about 10 Angstroms units, and moisture content of from about 20 to about 30 percent by weight water based on the weight of dry resin.

10. The process of claim 1 wherein the moisture content of the resin is controlled by a method comprising:
    (a) drying conventional water-swollen macroporous, sulfonic acid, cation exchange resin in a vacuum oven at 90° C. for several days, and
    (b) adding water to the dried resin so that the moisture content is in a range of from about 20 percent to about 30 percent weight of water based on dry resin.

* * * * *

UNITED STATES PATENT AND TRADEMARK OFFICE
CERTIFICATE OF CORRECTION

PATENT NO. : 4,277,637

DATED : July 7, 1981

INVENTOR(S) : Debra S. K. Kalmbach

It is certified that error appears in the above—identified patent and that said Letters Patent is hereby corrected as shown below:

Column 1, line 38, "sytrene" should read --styrene--.

Column 2, line 2, "α-alkylastyrene" should read --α-alkylstyrene--.

Column 2, line 37, "ar-arlkylstyrenes" should read --ar-alkylstyrenes--.

Column 2, line 38, "propylstryene" should read --propylstyrene--.

Column 2, line 51, "α-alkylstryene" should read --α-alkylstyrene--.

Column 3, line 2, "sulfonication" should read --sulfonation--.

Column 3, line 40, "stryene" should read --styrene--.

Column 3, line 57, "materials" should read --material--.

Column 5, line 22, "in" should read --is--.

Column 6, line 40, "Angstroms" should read --Angstrom--.

Signed and Sealed this

First Day of December 1981

[SEAL]

Attest:

GERALD J. MOSSINGHOFF

Attesting Officer

Commissioner of Patents and Trademarks